(12) United States Patent
Gono

(10) Patent No.: US 8,979,737 B2
(45) Date of Patent: Mar. 17, 2015

(54) CONTROL APPARATUS, BIO-OPTICAL MEASUREMENT APPARATUS AND ENDOSCOPE SYSTEM

(71) Applicant: Olympus Medical Systems Corp., Tokyo (JP)

(72) Inventor: Kazuhiro Gono, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/948,572

(22) Filed: Jul. 23, 2013

(65) Prior Publication Data

US 2014/0018623 A1 Jan. 16, 2014

Related U.S. Application Data

(63) Continuation of application No. PCT/JP2012/082943, filed on Dec. 19, 2012.

(60) Provisional application No. 61/597,313, filed on Feb. 10, 2012.

(51) Int. Cl.
*A61B 1/00* (2006.01)
*A61B 1/04* (2006.01)
(Continued)

(52) U.S. Cl.
CPC ......... *A61B 1/00002* (2013.01); *A61B 1/00006* (2013.01); *A61B 1/05* (2013.01)
USPC ........... 600/117; 600/118; 600/145; 600/109; 600/160

(58) Field of Classification Search
CPC .......... A61B 5/06; A61B 5/061; A61B 5/065; A61B 19/5244; A61B 1/00009
USPC ............. 600/117, 118, 109, 160, 110; 348/45
See application file for complete search history.

(56) References Cited

U.S. PATENT DOCUMENTS 4,588,294 A * 5/1986 Siegmund ...................... 600/117
4,986,262 A * 1/1991 Saito ............................. 600/108
(Continued)

FOREIGN PATENT DOCUMENTS

JP     A-06-304127     11/1994
JP     A-2005-319212     11/2005
(Continued)

OTHER PUBLICATIONS

Mar. 5, 2013 International Search Report issued in International Application No. PCT/JP2012/082943 (w/ English Translation).

*Primary Examiner* — Anhtuan T Nguyen
*Assistant Examiner* — William Chou
(74) *Attorney, Agent, or Firm* — Oliff PLC

(57) ABSTRACT

A control apparatus controls a bio-optical measurement apparatus which is configured to be inserted into a subject through an endoscopic device and is configured to perform an optical measurement of a biological tissue in the subject. The endoscopic device is configured to capture, by inserting a distal end part of the endoscopic device into the subject, in-vivo images of the subject by an imaging unit provided at the distal end part. The control apparatus includes a position determining unit configured to determine a position of the distal end part in the subject, and a permission signal outputting unit configured to output a permission signal for permitting the bio-optical measurement apparatus to perform the optical measurement based on a determination result by the position determining unit.

10 Claims, 14 Drawing Sheets

(51) Int. Cl.
*A61B 1/06* (2006.01)
*A61B 1/05* (2006.01)

(56) References Cited

U.S. PATENT DOCUMENTS 5,090,400 A * 2/1992 Saito .............................. 600/108
5,436,655 A * 7/1995 Hiyama et al. ................... 348/45
5,669,871 A * 9/1997 Sakiyama ..................... 600/117
2008/0242931 A1 * 10/2008 Nishino ......................... 600/117

FOREIGN PATENT DOCUMENTS

| JP | A-2006-223849 | 8/2006 |
| JP | A-2007-044491 | 2/2007 |
| JP | A-2011-206251 | 10/2011 |

* cited by examiner ical measurement to the bio-optical measurement apparatus based on a determination result by the position determining unit.

A bio-optical measurement apparatus according to another aspect of the present invention includes the above mentioned control apparatus, and a driving controller configured to control driving of the bio-optical measurement apparatus when accepting an input of the permission signal from the permission signal outputting unit.

An endoscope system according to another aspect of the present invention includes an endoscopic device configured to capture, by inserting a distal end part of the endoscopic device into a subject, in-vivo images of the subject by an imaging unit provided at the distal end part, and a bio-optical measurement apparatus that is configured to be inserted into the subject through the endoscopic device and is configured to perform an optical measurement of a biological tissue in the subject. The endoscopic device includes a position determining unit configured to determine a position of the distal end part in the subject, and a permission signal outputting unit configured to output a permission signal for permitting the optical measurement to the bio-optical measurement apparatus based on a determination result by the position determining unit.

The above and other features, advantages and technical and industrial significance of this invention will be better understood by reading the following detailed description of presently preferred embodiments of the invention, when considered in connection with the accompanying drawings.

US 8,979,737 B2

CONTROL APPARATUS, BIO-OPTICAL MEASUREMENT APPARATUS AND ENDOSCOPE SYSTEM

CROSS-REFERENCE TO RELATED APPLICATIONS

This application is a continuation of PCT international application Ser. No. PCT/JP2012/082943 filed on Dec. 19, 2012 which designates the United States, incorporated herein by reference, and which claims the benefit of priority from U.S. provisional application No. 61/597,313, filed on Feb. 10, 2012, incorporated herein by reference.

BACKGROUND OF THE INVENTION

1. Field of the Invention

The present invention relates to a control apparatus that controls an optical measurement performed by a bio-optical measurement apparatus that irradiates biological tissues with an illumination light and estimates a property of the biological tissues based on a measurement value of a detected light reflected or scattered from the biological tissues, relates to the bio-optical measurement apparatus, and relates to an endoscope system.

2. Description of the Related Art

Conventionally, a bio-optical measurement apparatus that irradiates biological tissues with an illumination light and estimates a property of the biological tissues based on a measurement value of a detected light reflected or scattered from the biological tissues has been known. The bio-optical measurement apparatus is used in combination with an endoscope that allows observing organs such as digestive organs. For example, there has been proposed a bio-optical measurement apparatus using a low-coherence enhanced backscattering (LEBS) technique in which biological tissues are irradiated with a low coherence white color light whose spatial coherence length is short from a distal end of an illumination fiber of a probe and frequency spectra of a plurality of scattered lights are measured by using a plurality of light receiving fibers to detect a property of the biological tissues.

Besides, a technique of using an imaging unit to capture in-vivo images, analyzing a blood vessel in the in-vivo images, and thereby measuring a blood component has been known (see Japanese Patent Application Laid-Open No. 2007-44491). It is possible in this technique to allow a user to easily recognize whether or not a blood vessel locates in an area suitable for imaging by generating an image of a blood vessel included in the in-vivo images and displaying the image of the blood vessel overlapped with the in-vivo images on a display monitor.

SUMMARY OF THE INVENTION

A control apparatus according to one aspect of the present invention controls a bio-optical measurement apparatus which is configured to be inserted into a subject through an endoscopic device and is configured to perform an optical measurement of a biological tissue in the subject. The endoscopic device is configured to capture, by inserting a distal end part of the endoscopic device into the subject, in-vivo images of the subject by an imaging unit provided at the distal end part. The control apparatus includes a position determining unit configured to determine a position of the distal end part in the subject, and a permission signal outputting unit configured to output a permission signal for permitting the

DETAILED DESCRIPTION OF THE PREFERRED EMBODIMENTS

Exemplary embodiments of a bio-optical measurement apparatus and an endoscope system according to the present invention will be explained in detail below by taking an endoscope system having a bio-optical measurement apparatus using an LEBS technique as an example with reference to the accompanying drawings. The present invention is not limited to the embodiments. The same part is assigned with the same reference symbol in the description of the drawings. It is necessary to note that the accompanying drawings are merely schematic and a relation between a thickness and a width of each member, a ratio of each member, and the like may be different from the reality. Besides, the dimensional relations and the ratio may be different from one drawing to another.

First Embodiment

Figure 1:
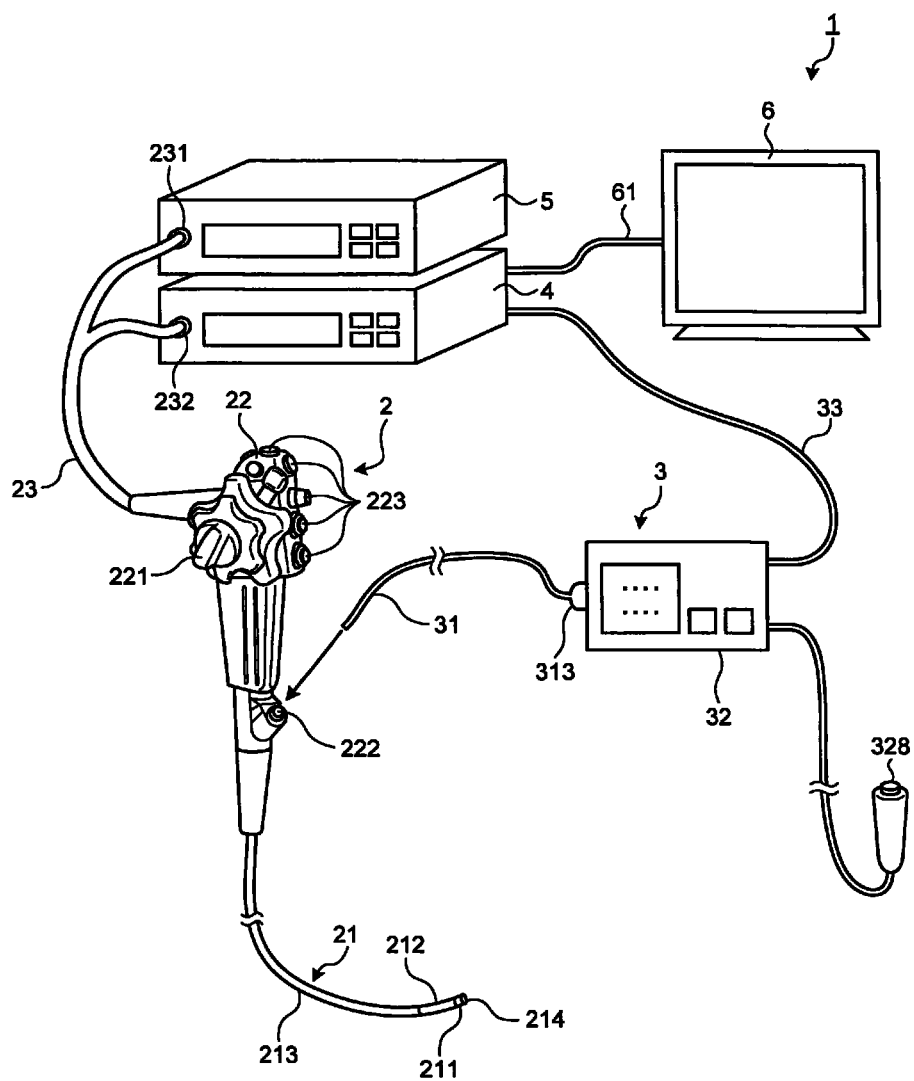
FIG. 1 schematically shows a configuration of an endoscope system according to a first embodiment of the present invention.

FIG. 1 schematically shows a configuration of an endoscope system according to a first embodiment of the present invention. As shown in FIG. 1, an endoscope system 1 according to the first embodiment includes an endoscopic device 2 (scope) that is configured to be inserted into a subject and is configured to capture in-vivo images of the subject to generate an image signal in the subject, a bio-optical measurement apparatus 3 that is configured to be inserted into the subject via the endoscopic device 2 and estimates a property of biological tissues in the subject, an illumination device 5 that generates an illumination light (observation light) for the endoscopic device 2, a processing device (processor) 4 that performs a specified image process on the signal of the image captured by the endoscopic device 2 and controls each unit of the endoscope system 1, and a display device 6 that displays the image corresponding to the image signal to which image processing is performed by the processing device 4.

The endoscopic device 2 includes an insertion unit 21, an operation unit 22 which is at a side of a base end part of the insertion unit 21 and grasped by an operator, and a universal cord 23 which has flexibility and extends from the operation unit 22.

The insertion unit 21 is realized by using an illumination fiber (light guide cable), an electrical cable, and the like. The insertion unit 21 includes a distal end part 211 including an imaging unit incorporating a CCD as an imaging element that captures images of the inside of the subject, a bend part 212 that is constituted by a plurality of bend pieces and can freely bend, and a flexible tube part 213 that has a flexibility and is provided at a base end side of the bend part 212. At the distal end part 211, provided are an illumination unit that illuminates the inside of the subject via an illumination lens, an observation unit that captures images of the inside of the subject, an opening part 214 that communicates with a treatment tool channel, and air feeding/water feeding nozzle (not shown).

The operation unit 22 includes a bend knob 221 that enables the bend part 212 to bend to a vertical direction and a horizontal direction, a treatment tool inserting part 222 through which treatment tools such as a biopsy forceps, a laser knife, and a measurement probe of the bio-optical measurement apparatus 3 are inserted to an inside of a body cavity of the subject, and a plurality of switches 223 by which the processing device 4, the illumination device 5, and peripheral equipment such as an air feeding device, a water feeding device, and a gas feeding device are operated. The treatment tool inserted from the treatment tool inserting part 222 comes out of the opening part 214 provided at the distal end of the insertion unit 21 by way of the treatment tool channel provided inside.

The universal cord 23 is configured by using an illumination fiber, an electrical cable, and the like. The universal cord 23 includes a connector part 231 which can be detachably attached to the illumination device 5 and a connector part 232 which can be detachably attached to the processing device 4. The universal cord 23 transmits an illumination light radiated from the illumination device 5 to the distal end part 211 via the connector part 231, the operation unit 22, and the flexible tube part 213. The universal cord 23 transmits the signal of the image captured by the imaging unit provided in the distal end part 211 to the processing device 4.

The bio-optical measurement apparatus 3 includes a measurement probe 31 that is inserted to the inside of the subject via the treatment tool inserting part 222 of the endoscopic device 2, a main body part 32 that radiates a measurement light to the measurement probe 31 and also receives at least one of light (reflection light) which comes through the measurement probe 31 and is returned from biological tissues (measurement target) and a scattered light to estimate a property of the biological tissues, and a transmission cable 33 that transmits a result of the measurement and the like by the main body part 32 to the processing device 4.

The processing device 4 performs a specified image process on the image signal of the inside of the subject, the image signal having been captured by the imaging unit in the distal end part 211 of the endoscopic device 2 and input via the universal cord 23. The processing device 4 records the result, input via the transmission cable 33, of the measurement by the bio-optical measurement apparatus 3. The processing device 4 controls each unit of the endoscope system 1 based on instruction signals of various kinds transmitted from the switches 223 in the operation unit 22 of the endoscopic device 2 via the universal cord 23.

The illumination device 5 is configured by using a white color light source, a condenser lens, and the like. The illumination device 5 supplies a white color light from the white color light source as an illumination light to the endoscopic device 2 connected via the illumination fiber of the universal cord 23.

The display device 6 is configured by using a displaying device using a liquid crystal or an organic electro luminescence (EL). The display device 6 displays an image corresponding to the image signal to which the specified image process is performed by the processing device 4, the result of the measurement by the bio-optical measurement apparatus 3, and the like via an image projection cable 61. This configuration allows the operator to operate the endoscopic device 2 while checking the images (in-vivo images) displayed in the display device 6, and thereby to observe a desired position in the inside of the subject and determine a property. This configuration also allows an assistant to observe the images displayed in the display device 6 and thereby to grasp an observation position of the endoscopic device 2 with respect to the subject.

Figure 2:
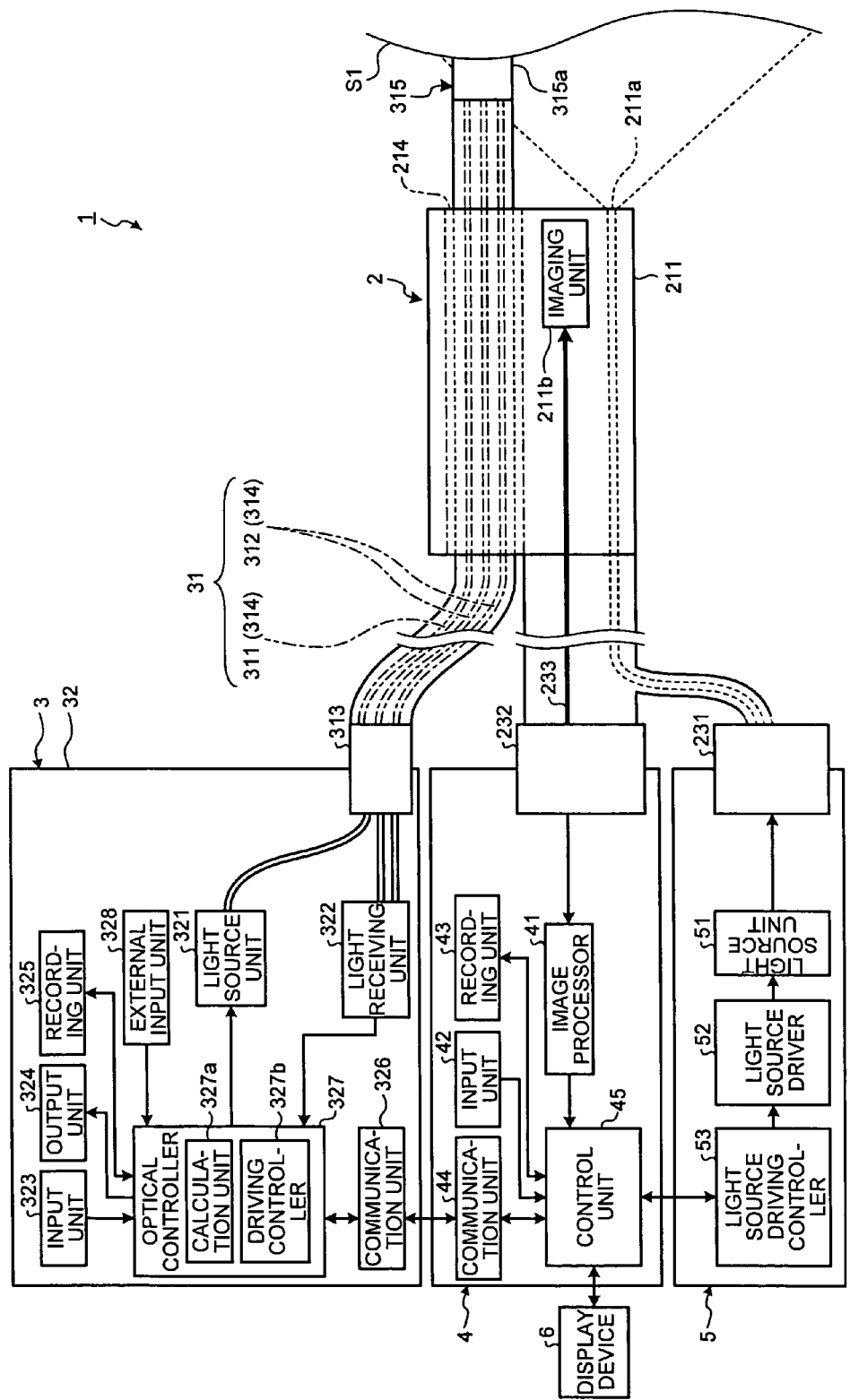
FIG. 2 is a block diagram showing a pattern of a configuration of the endoscope system according to the first embodiment of the present invention.

Next, a detailed configuration of the bio-optical measurement apparatus 3, the processing device 4, and the illumination device 5 explained with reference to FIG. 1 will be explained. FIG. 2 is a block diagram showing a pattern of a configuration of the endoscope system 1.

A detailed configuration of the bio-optical measurement apparatus 3 will be explained first. The bio-optical measurement apparatus 3 includes the measurement probe 31 and the main body part 32.

The measurement probe 31 is realized by using a plurality of optical fibers. For example, the measurement probe 31 is realized by using an illumination fiber 311 that radiates an illumination light to biological tissues S1 and a plurality of light receiving fibers 312 in which at least one of the reflection light reflected from the biological tissues and the scattered light are incident at different angles. The illumination fiber 311 and the light receiving fibers 312 are arranged in parallel with each other at least at their distal end parts. The measurement probe 31 includes a connector part 313, a flexible part 314, and a distal end part 315.

The connector part 313 is detachably connected to the main body part 32. The connector part 313 radiates the illumination light radiated from the main body part 32 to the measurement probe 31 and also radiates at least one of the reflection light incident via the measurement probe 31 and the scattered light to the main body part 32.

The flexible part 314 has a flexibility, transmits the illumination light radiated from the main body part 32 to the distal end part 315 including a distal end where end surface of the illumination fiber 311 is exposed, and transmits at least one of the reflection light incident via the distal end part 315 and the scattered light to the main body part 32.

The illumination light transmitted from the flexible part 314 is radiated on the biological tissues S1 and at least one of the reflection light reflected on the biological tissues S1 and the scattered light are incident in the distal end part 315. The distal end part 315 includes a rod 315a having a permeability as an optical member. The rod 315a has a circular cylindrical shape so that a distance between a surface of the biological tissues S1 and distal ends of the illumination fiber 311 and the light receiving fibers 312 becomes fixed. While the measurement probe 31 having two light receiving fibers 312 is taken as an example and explained in FIG. 2, two or more light receiving fibers 312 may be provided since it is only necessary to receive scattered lights of at least two kinds whose scattering angles are different. Besides, it is only necessary that at least one illumination fiber 311 is provided.

The main body part 32 includes a light source unit 321, a light receiving unit 322, an input unit 323, an output unit 324, a recording unit 325, a communication unit 326, an optical controller 327, and an external input unit 328.

The light source unit 321 is realized by a white color light emitting diode (LED), an incoherent light source such as a xenon lamp and a laser, and at least one lens if need arises. The light source unit 321 irradiates the biological tissues S1 with the illumination light via the connector part 313 and the measurement probe 31.

The light receiving unit 322 performs a measurement by receiving at least one of the light which is irradiated from the measurement probe 31 and reflected on the biological tissues S1 and the scattered light. The light receiving unit 322 is realized by using a plurality of spectrometers. Specifically, the spectrometer of the light receiving unit 322 is provided depending on the number of the light receiving fibers 312. The light receiving unit 322 measures a spectrum component and an intensity distribution of at least one of the reflection light irradiated from the measurement probe 31 and the scattered light to measure each wavelength. The light receiving unit 322 outputs a result of the measurement to the optical controller 327.

The input unit 323 is realized by using a touch tone switch, a touch screen, and the like and performs an output in response to an input of a start-up signal for instructing a start of the bio-optical measurement apparatus 3 or operation signals for instructing other operations of various kinds.

The output unit 324 is realized by a displaying device such as a liquid crystal display and an organic EL display, a speaker, and the like, and outputs information concerning processes of various kinds in the bio-optical measurement apparatus 3.

The recording unit 325 is realized by using a volatile memory and a non-volatile memory and records various programs for operating the bio-optical measurement apparatus 3, and data and parameters of various kinds used in an optical measuring process. The recording unit 325 temporarily records information in process in the bio-optical measurement apparatus 3. The recording unit 325 records the result of the measurement of the bio-optical measurement apparatus 3.

The communication unit 326 is a communication interface that allows performing a communication with the processing device 4 via the transmission cable 33. The communication unit 326 transmits the result of the measurement of the bio-optical measurement apparatus 3 to the processing device 4 and also outputs an instruction signal and a control signal transmitted from the processing device 4 to the optical controller 327.

The optical controller 327 is configured by using a central processing unit (CPU) and the like. The optical controller 327 controls a processing operation of each unit in the bio-optical measurement apparatus 3. The optical controller 327 controls the operation of the bio-optical measurement apparatus 3 by performing a transmission and the like of data and information instructing each component of the bio-optical measurement apparatus 3. The optical controller 327 records the result of the measurement by the light receiving unit 322 in the recording unit 325. The optical controller 327 includes a calculation unit 327a and a driving controller 327b.

The calculation unit 327a performs a plurality of calculation processes based on the result of the measurement by the light receiving unit 322 and calculates a characteristic value concerning the property of the biological tissues S1. A type of the characteristic value is set according to the instruction information that the input unit 323 has accepted.

The driving controller 327b performs a control of driving the bio-optical measurement apparatus 3 when receiving a permission signal, input from the external input unit 328, of permitting an optical measurement. Specifically, the driving controller 327b enables the optical measurement of the bio-optical measurement apparatus 3 by driving the light source unit 321 and the light receiving unit 322.

The external input unit 328 is configured by using a remote switch such as a pull switch. The external input unit 328 is connected to the bio-optical measurement apparatus 3 and accepts the input of the permission signal (a trigger of the measurement) for permitting the bio-optical measurement apparatus 3 to perform the optical measurement. Specifically, the external input unit 328, by being operated by an assistant other than an operator who operates the endoscopic device 2, outputs the permission signal for permitting the bio-optical measurement apparatus 3 to perform the optical measurement. In the first embodiment, the external input unit 328 and the bio-optical measurement apparatus 3 may be connected wirelessly, for example, via infrared communication in a manner of allowing a two-way communication therebetween. Moreover, a recording unit that records biometric information (fingerprints and vein) of the operator and the assistant, a reader that reads the biometric information of the operator and the assistant, and a determining unit that determines consistency between the biometric information read by the reader and the biometric information recorded by the recording unit may be provided in the external input unit 328, and an operation input via the external input unit 328 may be accepted depending on the result by the determining unit.

The processing device 4 will be explained next. The processing device 4 includes an image processor 41, an input unit 42, and a recording unit 43, a communication unit 44, and a control unit 45.

The image processor 41 obtains, via the connector part 232 and an image projection cable 233, an image signal which is a digital signal captured by the imaging unit 211b arranged in the vicinity of an observation window (not shown) of the distal end part 211 and performs a specified image process on the obtained image signal. Specifically, the image processor 41 performs image processes including at least an optical black subtraction process, a white balance (WB) adjustment process, a synchronization process of the image signal in a case where the imaging element has a Bayer pattern, a color matrix computing process, a gamma correction process, a color reproduction process, an edge emphasis process, and the like on the image signal (image data). The image processor 41 converts the image signal to which the image processes are performed from a digital signal into an analogue signal and changes the converted analogue image signal to have a format such as a high resolution digital television system. The image processor 41 outputs the image signal to the display device 6 via the control unit 45. Thus, one in-vivo image is displayed in the display device 6.

The input unit 42 is realized by using operation devices such as a mouse, a keyset, and a touch screen and accepts an input of instruction information of various kinds of the endoscope system 1. Specifically, the input unit 42 accepts an input of subject information (ID, date of birth, name, and the like, for example), identification information of the endoscopic device 2 (ID and examination item, for example), and instruction information of various kinds such as an examination content.

The recording unit 43 is realized by a volatile memory and a non-volatile memory and records various programs for operating the processing device 4 and the illumination device 5. The recording unit 43 temporarily records information in process in the processing device 4. The recording unit 43 records the image signal to which the image processes are performed by the image processor 41 and the result of the measurement by the bio-optical measurement apparatus 3. The recording unit 43 may be configured by using a memory card and the like to be attached externally to the processing device 4.

The communication unit 44 is a communication interface that allows performing a communication with the bio-optical measurement apparatus 3 via the transmission cable 33.

The control unit 45 is realized by using a CPU and the like. The control unit 45 controls a processing operation of each unit of the processing device 4. The control unit 45 controls the operation of the processing device 4 by performing a transmission and the like of data and information instructing each component of the processing device 4. The control unit 45 is connected to the endoscopic device 2, the bio-optical measurement apparatus 3, and the illumination device 5 by respective cables.

The illumination device 5 will be explained next. The illumination device 5 includes a light source unit 51, a light source driver 52, and a light source driving controller 53.

The light source unit 51 is configured by using a white color LED, a xenon lamp, or the like. The light source unit 51 generates an illumination light to be supplied to the endoscopic device 2.

The light source driver 52 supplies a specified electric power to the light source unit 51 under the control of the light source driving controller 53. Thus, the light emitted from the light source unit 51 is radiated on the biological tissues S1 from an illumination part 211a of the distal end part 211 of the insertion unit 21 via the connector part 231 and the universal cord 23.

The light source driving controller 53 is realized by using a CPU and the like and controls the light source driver 52 based on the instruction signal input from the processing device 4.

Figure 3:
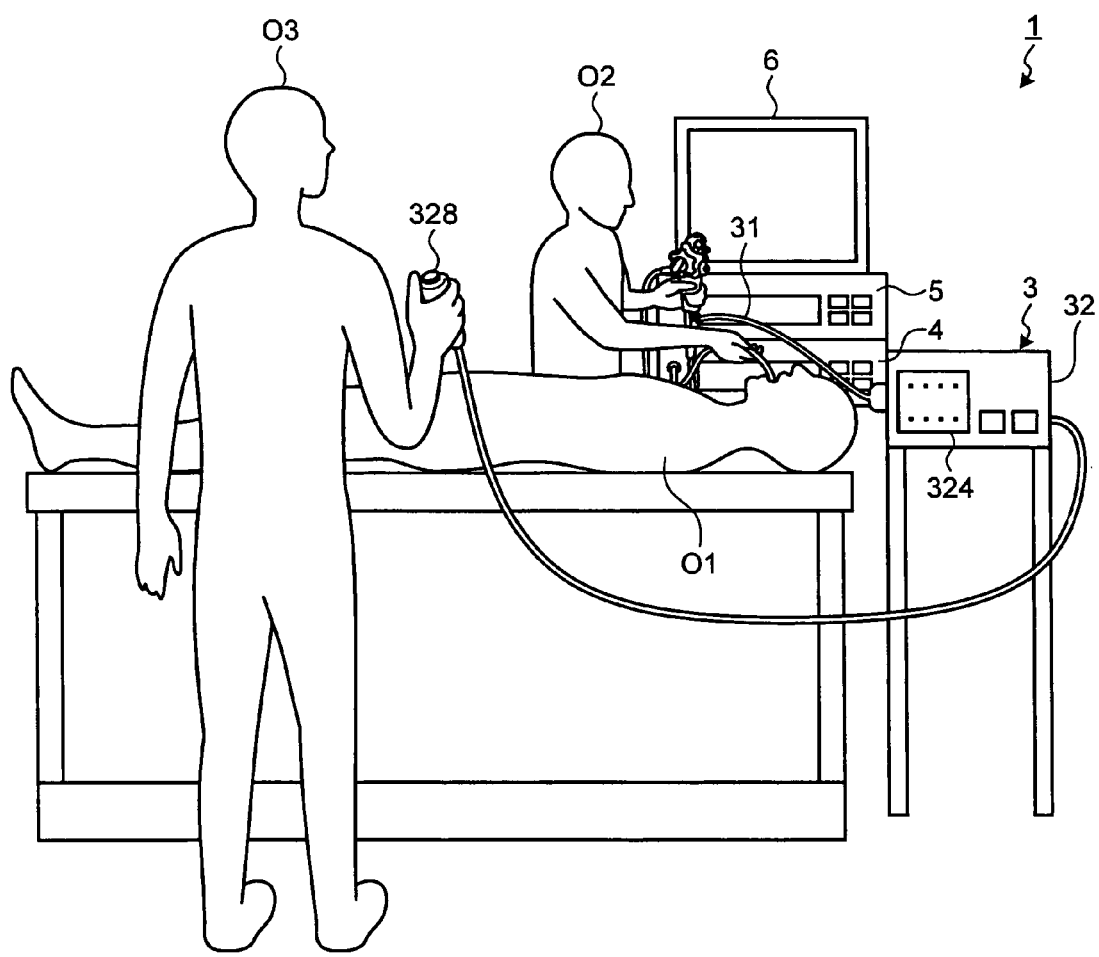
FIG. 3 is a pattern diagram of a situation where an operator performs an examination on a subject by using the endoscope system according to the first embodiment of the present invention.
Figure 4:
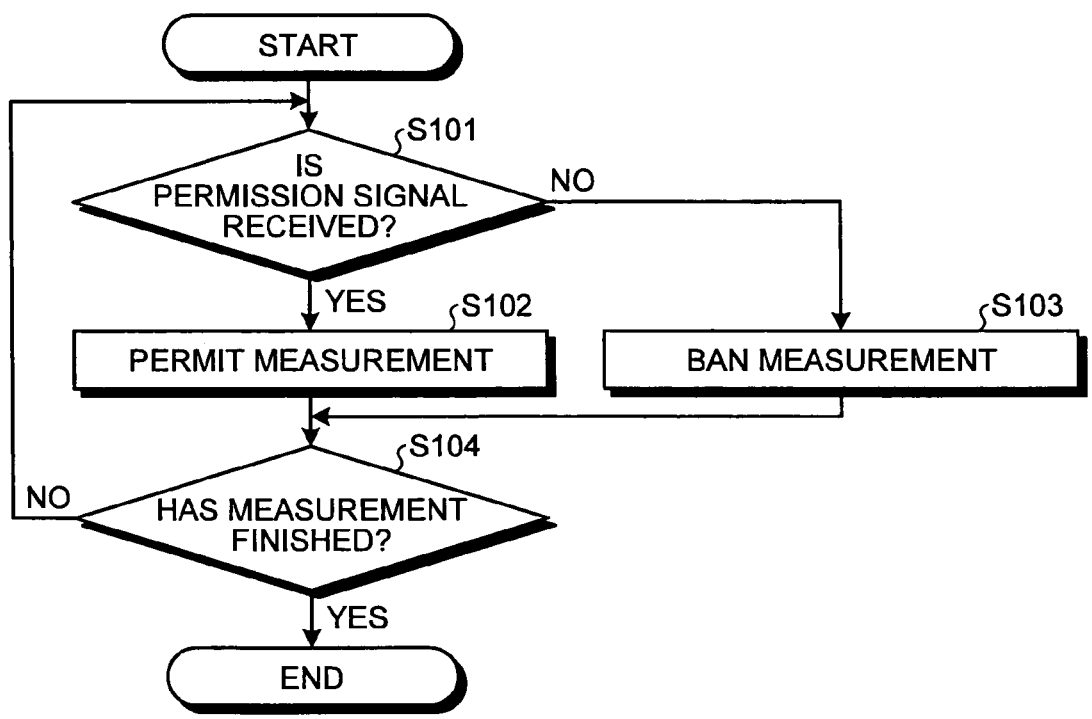
FIG. 4 is a flowchart of an outline of a process performed by a bio-optical measurement apparatus in the endoscope system according to the first embodiment of the present invention.

A process performed by the bio-optical measurement apparatus 3 in the endoscope system 1 configured as described above will be explained. FIG. 3 is a pattern diagram of a situation where an operator performs an examination on a subject by using the endoscope system 1. FIG. 4 is a flowchart of an outline of a process performed by the bio-optical measurement apparatus 3 in the endoscope system 1.

As shown in FIG. 4, the optical controller 327 determines whether or not the permission signal of permitting the optical measurement is input from the external input unit 328 (step S101). Specifically, an assistant O3 (nurse) operates, by observing in-vivo images of a subject O1 (patient) sequentially displayed in the display device 6, the external input unit 328 when the distal end part 211 of the endoscopic device 2 operated by an operator O2 (doctor) reaches a specified organ (a duodenum or a stomach, for example) in the subject O1, as shown in FIG. 3. Under this situation, the optical controller 327 determines whether or not the permission signal for permitting the bio-optical measurement apparatus 3 to perform the optical measurement is input. When the permission signal is input ("Yes" at step S101), the optical controller 327 enables the optical measurement by the bio-optical measurement apparatus 3 (step S102). Specifically, the driving controller 327b drives the light source unit 321 and the light receiving unit 322. On this occasion, the driving controller 327b may control the output unit 324 to output a sound, an indication, and the like to the effect that the optical measurement by the bio-optical measurement apparatus 3 is enabled.

On the other hand, when the permission signal is not input ("No" at step S101), the optical controller 327 bans the optical measurement by the bio-optical measurement apparatus 3 (step S103). Specifically, the driving controller 327b does not drive the light source unit 321 and the light receiving unit 322. In this situation, the driving controller 327b may control the output unit 324 to give warning by a sound, an indication, and the like to the effect that the optical measurement by the bio-optical measurement apparatus 3 cannot be performed when a signal of starting the optical measurement by the bio-optical measurement apparatus 3 is input from the input unit 323.

The optical controller 327 then determines whether or not the optical measurement has finished (step S104). Specifically, the optical controller 327 determines whether or not an instruction signal instructing a finish of the optical measurement is input from the input unit 323. When the optical controller 327 determines that the optical measurement has finished ("Yes" at step S104), the bio-optical measurement apparatus 3 ends the process. On the other hand, when the optical controller 327 determines that the optical measurement has not finished ("No" at step S104), the bio-optical measurement apparatus 3 returns to step S101.

In the first embodiment described above, the driving controller 327b performs a control of enabling the optical measurement by the bio-optical measurement apparatus 3 when receiving the permission signal of permitting the optical measurement by the bio-optical measurement apparatus 3 input from the external input unit 328. Thus, it is possible to perform a measurement only at an appropriate site (a stomach and a duodenum, for example) in a biological body and to surely prevent a human error.

While the optical measurement is enabled by driving the light source unit 321 and the light receiving unit 322 of the bio-optical measurement apparatus 3 when the driving controller 327b receives the permission signal, a flag to the effect that a computing result of the optical measurement obtained by the calculation unit 327a is valid may be added and recorded in the recording unit 325, for example. Thus, it is possible to determine whether or not the measurement is performed surely at an appropriate site in a biological body in a case where a person other than an operator performs a medical examination of a subject by using the measurement result of the bio-optical measurement apparatus 3 at a different site.

Second Embodiment

A second embodiment of the present invention will be explained next. An endoscope system according to the second embodiment has a difference in the configuration and the process in the control apparatus in the endoscope system described above. Therefore, after a configuration of a control apparatus of an endoscope system according to the second embodiment is explained, a process performed by the endoscope system according to the second embodiment will be explained below. The same component is assigned with the same reference symbol and the explanation thereof will be omitted.

Figure 5:
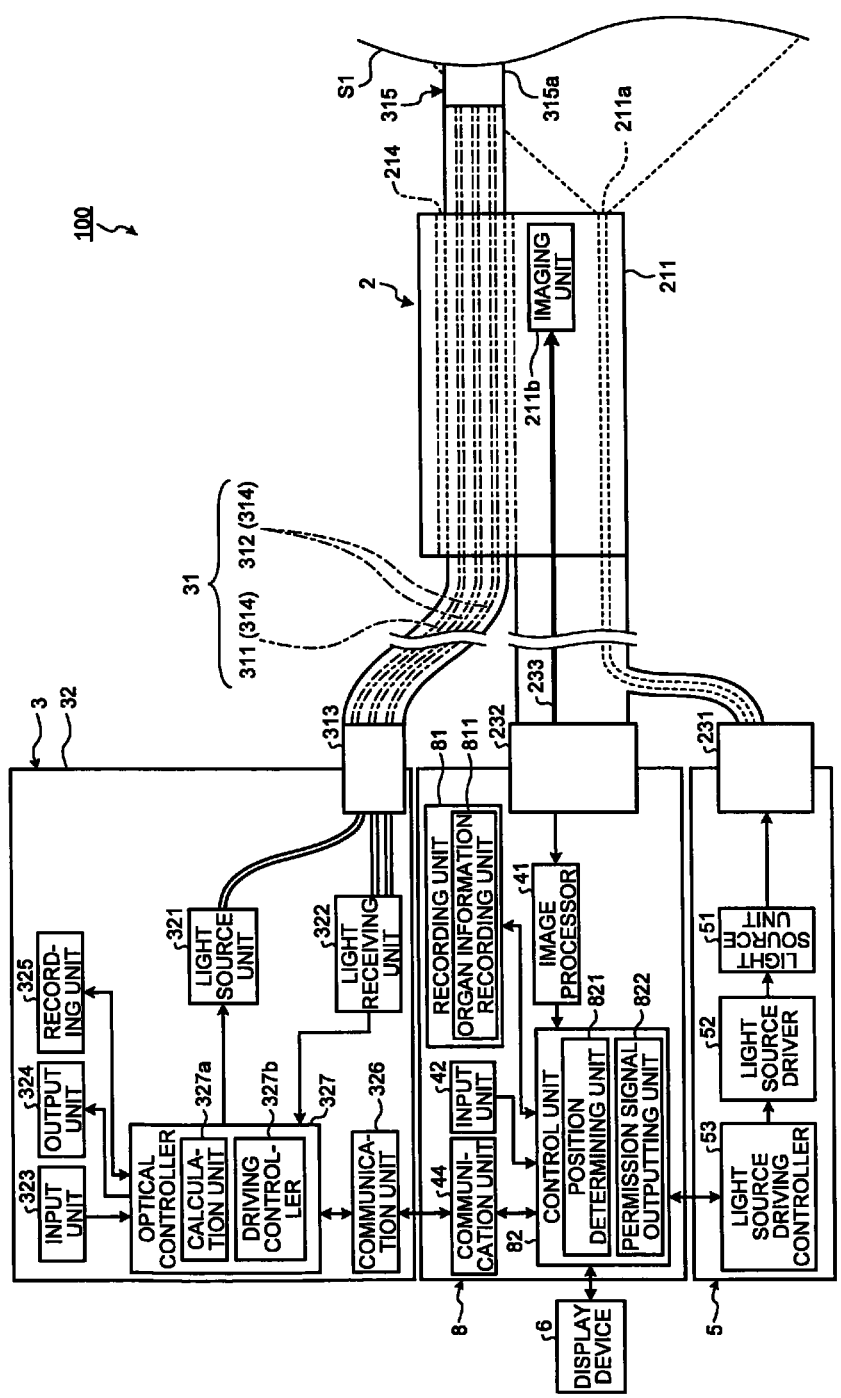
FIG. 5 is a block diagram showing a pattern of a configuration of an endoscope system according to a second embodiment of the present invention.

FIG. 5 is a block diagram showing a pattern of a configuration of an endoscope system 100 according to the second embodiment. As shown in FIG. 5, the endoscope system 100 includes the bio-optical measurement apparatus 3, the illumination device 5, the display device 6, and a processing device 8.

The processing device 8 includes the image processor 41, the input unit 42, the communication unit 44, a recording unit 81, and a control unit 82.

The recording unit 81 is realized by using a volatile memory and a non-volatile memory and records various programs for operating the processing device 8 and the illumination device 5. The recording unit 81 temporarily records information in process in the processing device 8. The recording unit 81 includes an organ information recording unit 811. The organ information recording unit 811 records image information of a characteristic part, a pylorus of a duodenum for example, at a boundary of organs which is set in advance and used when the control unit 82 to be described later performs a determination on an in-vivo image corresponding to an image signal to which the image processes are performed by the image processor 41 by a pattern matching.

The control unit 82 is realized by using a CPU and the like. The control unit 82 controls a processing operation of each unit of the processing device 8. The control unit 82 includes a position determining unit 821 and a permission signal outputting unit 822.

Figure 6A:
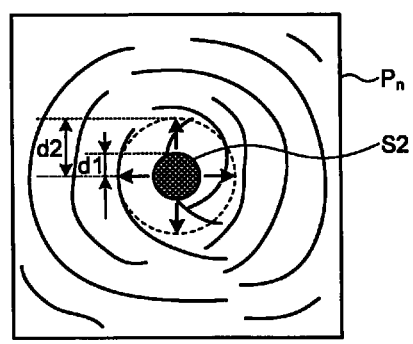
FIG. 6A is an explanatory view of an outline of a determination method by a position determining unit in the endoscope system according to the second embodiment of the present invention.
Figure 6B:
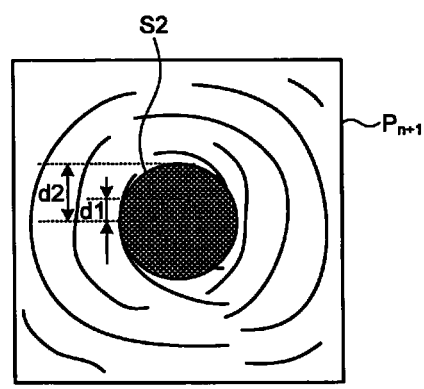
FIG. 6B is an explanatory view of an outline of a determination method by the position determining unit in the endoscope system according to the second embodiment of the present invention.

The position determining unit 821 obtains, via the image processor 41, an image signal captured by the imaging unit 211b and determines the position of the distal end part 211 of the endoscopic device 2 in the inside of the subject based on the in-vivo image corresponding to the obtained image signal. Specifically, the position determining unit 821 obtains the image signal captured by the imaging unit 211b via the image processor 41, performs a pattern matching with respect to the in-vivo image corresponding to the obtained image signal by using image information recorded in the organ information recording unit 811, and thereby determines whether or not the distal end part 211 of the endoscopic device 2 has reached a specified organ. For example, the position determining unit 821 determines a boundary between the stomach and the duodenum with respect to the in-vivo image corresponding to the image signal captured by the imaging unit 211b and thereby determines whether or not the distal end part 211 of the endoscopic device 2 has reached the duodenum. Specifically, as shown in FIGS. 6A and 6B, by performing a pattern matching with respect to an image $P_n$ (n=positive integer) captured by the imaging unit 211b in a continuous manner by using image information recorded in the organ information recording unit 811, the position determining unit 821 determines that the distal end part 211 of the endoscopic device 2 has reached the duodenum when a size of a pylorus S2 included in the image $P_n$ becomes a specified size, from a width d1 in FIG. 6A to a width d2 in FIG. 6B, for example. By changing image information recorded in the organ information recording unit 811 depending on an instruction signal input from the input unit 42, the position determining unit 821 is able to arbitrarily change a boundary of organs to be determined. While the position determining unit 821 determines whether or not the distal end part 211 of the endoscopic device 2 has reached the duodenum depending on a change in shape of the pylorus S2 in FIGS. 6A and 6B, the determination may be made depending on a shape of any other part.

The permission signal outputting unit 822 outputs the permission signal for permitting the optical measurement to the bio-optical measurement apparatus 3 based on the result of the determination by the position determining unit 821. Specifically, the permission signal outputting unit 822 outputs to the bio-optical measurement apparatus 3 the permission signal of permitting the optical measurement when the position determining unit 821 determines that the distal end part 211 of the endoscopic device 2 has reached an organ set in advance, the duodenum for example. Therefore, the control unit 82 including the position determining unit 821 and the permission signal outputting unit 822 serves as a control apparatus that outputs the permission signal to the bio-optical measurement apparatus 3 in the second embodiment.

Figure 7:
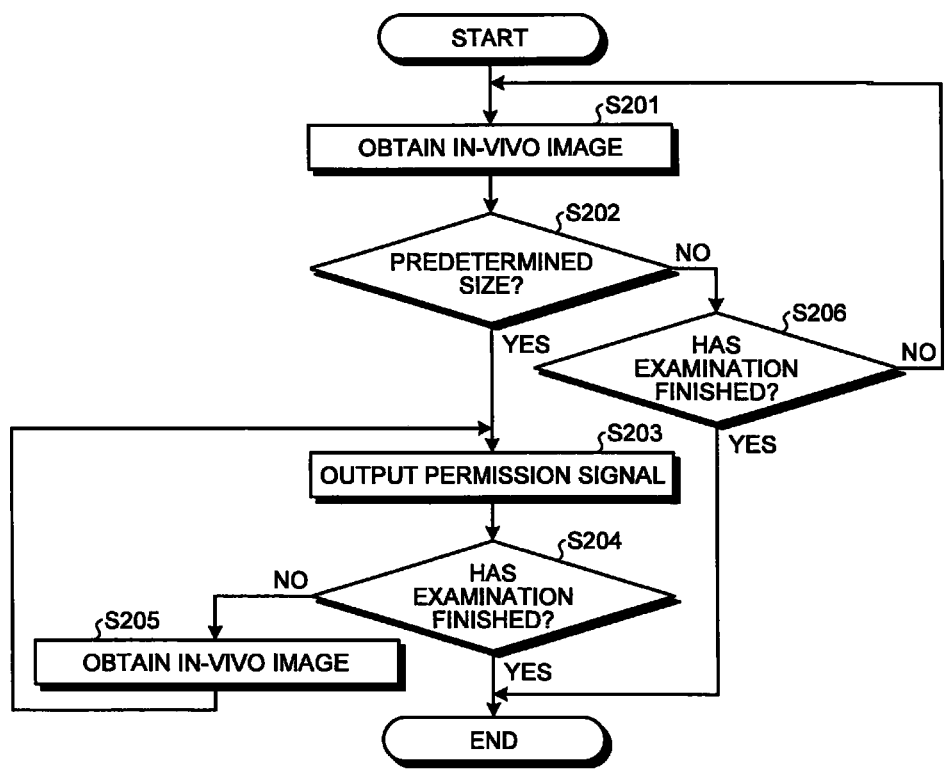
FIG. 7 is a flowchart of an outline of a process performed by a processing device in the endoscope system according to the second embodiment of the present invention.

A process performed by the processing device 8 in the endoscope system 100 configured as described above will be explained. FIG. 7 is a flowchart of an outline of a process performed by the processing device 8 in the endoscope system 100.

As shown in FIG. 7, the control unit 82 obtains an in-vivo image generated via the image processes by the image processor 41 on the image signal captured by the imaging unit 211b (step S201).

The position determining unit 821 then determines whether or not a specified organ, a pylorus for example, becomes a specified size by performing a pattern matching with respect to the in-vivo image (step S202). When the position determining unit 821 determines that the pylorus becomes the specified size ("Yes" at step S202), the process in the endoscope system 100 moves to step S203 to be described later. On the other hand, when the position determining unit 821 determines that the pylorus does not become the specified size ("No" at step S202), the process in the endoscope system 100 moves to step S206 to be described later.

At step S203, the permission signal outputting unit 822 outputs the permission signal for permitting the optical measurement to the bio-optical measurement apparatus 3 (step S203). In response to the permission signal, the driving controller 327b of the bio-optical measurement apparatus 3 drives the light source unit 321 and the light receiving unit 322 to enable the optical measurement.

The control unit 82 then determines whether or not the endoscopic examination has finished (step S204). Specifically, the control unit 82 determines whether or not an instruction signal instructing a finish of the examination is input from the input unit 42. When the control unit 82 determines that the endoscopic examination has finished ("Yes" at step S204), the processing device 8 ends the process. On the other hand, when the endoscopic examination has not finished ("No" at step S204), the control unit 82 obtains an in-vivo image generated via the image processes by the image processor 41 on the image signal captured by the imaging unit 211b (step S205) and the processing device 8 returns to step S203.

When the position determining unit 821 determines that the pylorus does not become the specified size at step S202 ("No" at step S202), the control unit 82 determines whether or not the endoscopic examination has finished (step S206). When the control unit 82 determines that the endoscopic examination has finished ("Yes" at step S206), the processing device 8 ends the process. On the other hand, when the control unit 82 determines that the endoscopic examination has not finished ("No" at step S206), the processing device 8 returns to step S201.

According to the second embodiment of the present invention described above, the permission signal outputting unit 822 outputs the permission signal for permitting the optical measurement to the bio-optical measurement apparatus 3 when the position determining unit 821 determines that the distal end part 211 of the endoscopic device 2 has reached a specified organ. Thus, it is possible to automatically perform a measurement only at an appropriate site in a biological body and to surely prevent a human error.

While the optical measurement is enabled by driving the light source unit 321 and the light receiving unit 322 of the bio-optical measurement apparatus 3 when the driving controller 327b receives the permission signal for the measurement from the permission signal outputting unit 822 via the communication unit 44 and the communication unit 326 in the second embodiment, a flag to the effect that a computing result of the optical measurement obtained by the calculation unit 327a is valid may be added and recorded in the recording unit 325. Thus, it is possible to determine whether or not the measurement is performed at an appropriate site in a case where an operator and a person other than the operator perform a medical examination of a subject by using the measurement result of the bio-optical measurement apparatus 3 at a different site.

While the position determining unit 821 and the permission signal outputting unit 822 are provided in the control unit 82 of the processing device 8 in the second embodiment, they may be provided in the bio-optical measurement apparatus 3. This configuration allows performing the measurement at an appropriate site only by the bio-optical measurement apparatus 3.

Third Embodiment

A third embodiment of the present invention will be explained next. An endoscope system according to the third embodiment has a difference in the configuration of the illumination device in the endoscope system described above. Therefore, after a configuration of an illumination device in an endoscope system according to the third embodiment is explained, a process performed by the endoscope system according to the third embodiment will be explained. The same component is assigned with the same reference symbol in the explanation.

Figure 8:
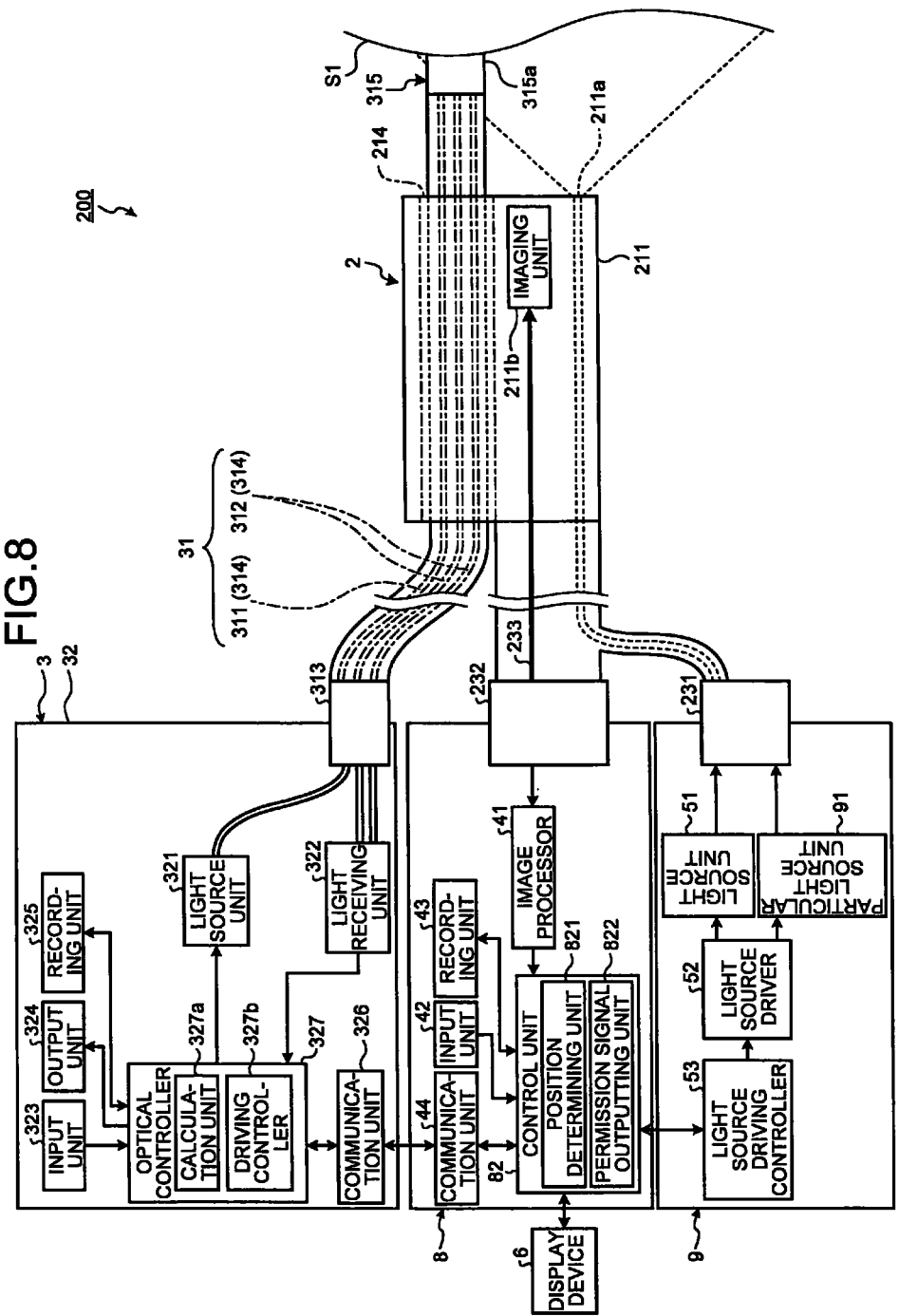
FIG. 8 is a block diagram showing a pattern of a configuration of an endoscope system according to a third embodiment of the present invention.

FIG. 8 is a block diagram showing a pattern of a configuration of an endoscope system 200 according to the third embodiment. As shown in FIG. 8, the endoscope system 200 includes the bio-optical measurement apparatus 3, the display device 6, the processing device 8, and an illumination device 9.

The illumination device 9 includes the light source unit 51, the light source driver 52, the light source driving controller 53, and a particular light source unit 91.

The particular light source unit 91 generates, as a particular light, light whose wavelength band is different from the white color illumination light and which has green (G) and blue (B) color components whose band is narrowed by a narrow band-pass filter. The particular light to be generated by the particular light source unit 91 may be, for example, a narrow band imaging (NBI) illumination light of two bands, i.e., a blue color light (400 to 500 nm, for example) and a green color light (500 to 600 nm, for example), and the like, the bands being narrowed to be easily absorbed by hemoglobin in blood, for example. In the third embodiment, the particular light source unit 91 generates the NBI illumination light as a particular light.

Figure 9:
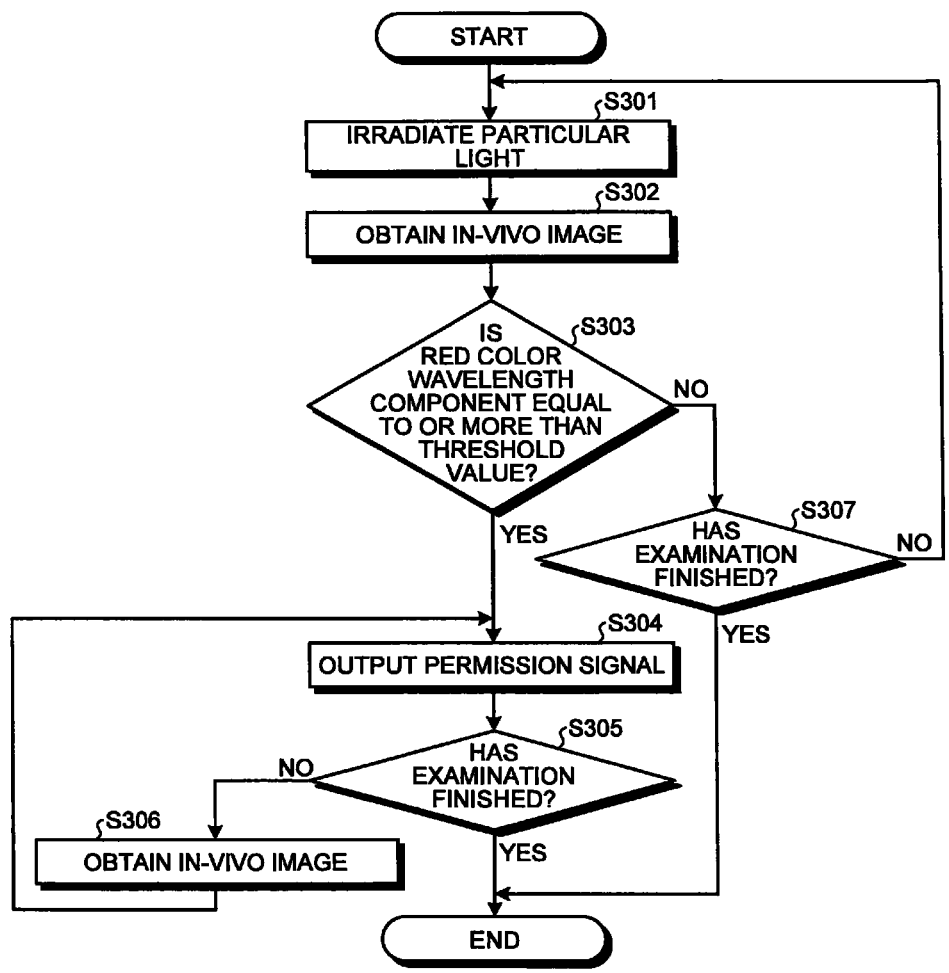
FIG. 9 is a flowchart of an outline of a process performed by a processing device in the endoscope system according to the third embodiment of the present invention.

A process performed by the processing device 8 in the endoscope system 200 configured as described above will be explained. FIG. 9 is a flowchart of an outline of a process performed by the processing device 8 in the endoscope system 200.

As shown in FIG. 9, the control unit 82 controls the illumination device 9 to radiate the particular light (step S301). Specifically, the control unit 82 outputs a driving signal of driving the particular light source unit 91 to the light source driving controller 53. Thus, it is possible to illuminate the inside of the biological body of the subject with the NBI illumination light in the endoscope system 200.

The control unit 82 then obtains an in-vivo image generated via the image processes by the image processor 41 on the image signal captured by the imaging unit 211b (step S302).

After that, the position determining unit 821 determines whether or not a red color luminance component included in the in-vivo image exceeds a threshold value (step S303). Specifically, the position determining unit 821 determines whether or not a wavelength component specific to an organ as a measurement target included in the in-vivo image, for example, the red color luminance component which is a wavelength component included in the in-vivo image in the measurement in the duodenum since bile is contained in a duodenal mucosa and shows a bright red color in the NBI (NBI illumination light), exceeds the threshold value. Bile is contained in a duodenal mucosa and shows a bright red color in NBI (NBI illumination light). When the position determining unit 821 determines that the red color luminance component included in the in-vivo image exceeds the threshold value ("Yes" at step S303), the processing device 8 moves to step S304. On the other hand, when the red color luminance component included in the in-vivo image does not exceed the threshold value ("No" at step S303), the processing device 8 moves to step S307.

Steps S304 to S307 respectively correspond to steps S203 to S206 in FIG. 7.

According to the third embodiment of the present invention described above, the permission signal outputting unit 822 outputs the permission signal for permitting the optical measurement to the bio-optical measurement apparatus 3 when the position determining unit 821 determines that the wavelength component specific to an organ as a measurement target included in the in-vivo image exceeds the threshold value set in advance. Thus, it is possible to automatically perform a measurement only at an appropriate site in a biological body and to surely prevent a human error.

While the optical measurement is enabled by driving the light source unit 321 and the light receiving unit 322 of the bio-optical measurement apparatus 3 when the driving controller 327b receives the permission signal for the measurement, a flag to the effect that a computing result of the optical measurement obtained by the calculation unit 327a is valid may be added and recorded in the recording unit 325. Thus, it is possible to determine whether or not the measurement is performed at an appropriate site in a case where an operator performs a medical examination of a subject by using the measurement result of the bio-optical measurement apparatus 3 at a different site.

While the position determining unit 821 and the permission signal outputting unit 822 are provided in the control unit 82 of the processing device 8 in the third embodiment, they may be provided in the bio-optical measurement apparatus 3. This configuration allows surely performing the measurement at an appropriate site only by the bio-optical measurement apparatus 3.

Fourth Embodiment

A fourth embodiment of the present invention will be explained next. An endoscope system according to the fourth embodiment has a difference in the configuration of the insertion unit and the control apparatus in the endoscopic device in the endoscope system described above and is further provided with an endoscope insertion shape observing device that observes a shape and a position of an insertion unit of an endoscope. Therefore, reference will be made below to an insertion unit, a control apparatus, and the endoscope insertion shape observing device in an endoscopic device in an endoscope system according to the fourth embodiment. The same component is assigned with the same reference symbol in the explanation.

Figure 10:
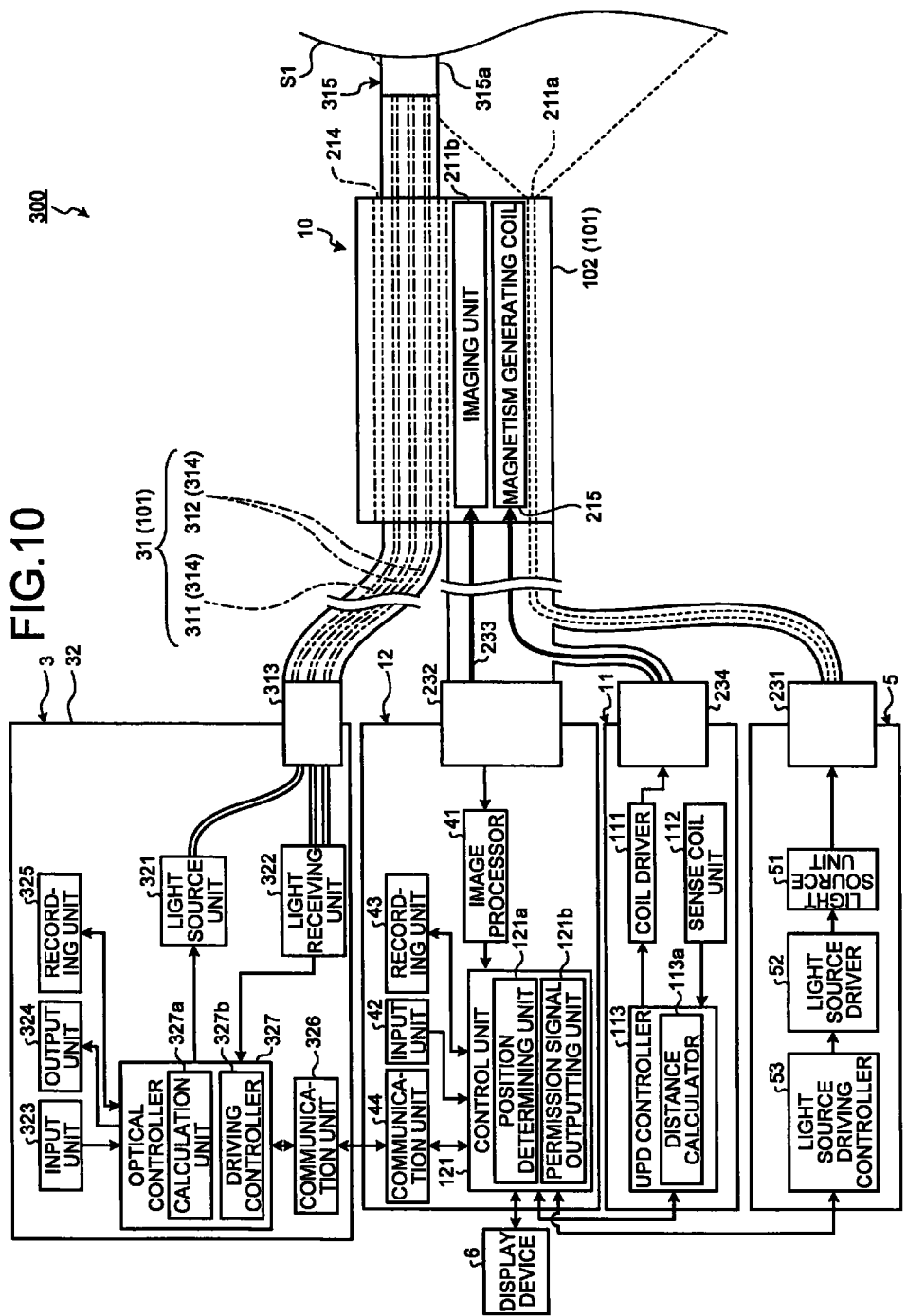
FIG. 10 is a block diagram showing a pattern of a configuration of an endoscope system according to a fourth embodiment of the present invention.

FIG. 10 is a block diagram showing a pattern of a configuration of an endoscope system 300 according to the fourth embodiment. As shown in FIG. 10, the endoscope system 300 includes an endoscopic device 10, an endoscope insertion shape observing device 11 (hereinafter referred to as a "UPD device 11"), and a processing device 12.

The endoscopic device 10 includes an insertion unit 101 instead of the insertion unit 21 in the first to the fourth embodiments described above. The insertion unit 101 is inserted to an inside of a subject. The insertion unit 101 includes the imaging unit 211b, a magnetism generating coil 215, and a connector part 234 at a distal end part 102.

The magnetism generating coil 215 is realized by a magnetism generating coil that generates magnetism. A plurality of magnetism generating coils 215 are arranged at specified intervals with respect to the insertion unit 101.

The UPD device 11 includes a coil driver 111, a sense coil unit 112, and a UPD controller 113. The UPD device 11 is arranged in the vicinity of the subject.

The coil driver 111 causes the magnetism generating coil 215 to generate a magnetic field by applying thereto, via the connector part 234, a driving signal of a specified frequency under the control of the UPD controller 113.

The sense coil unit 112 is configured by a plurality of sense coils which are arranged in a specified positional relation for sensing the magnetic field and senses respective positions of the magnetism generating coils 215.

The UPD controller 113 is realized by using a CPU and the like and controls each unit of the UPD device 11. The UPD controller 113 includes a distance calculator 113a.

The distance calculator 113a calculates a distance of the distal end part 102 of the insertion unit 101 based on a signal sensed by the sense coil unit 112. Specifically, the distance calculator 113a calculates a distance from a specified position, for example, a mouth or an anus of the subject to a position to which the distal end part 102 of the insertion unit 101 is inserted based on the signal sensed by the sense coil unit 112.

The processing device 12 includes the image processor 41, the input unit 42, the recording unit 43, the communication unit 44, and a control unit 121.

The control unit 121 is realized by using a CPU and the like. The control unit 121 controls a processing operation of each unit of the processing device 12. The control unit 121 includes a position determining unit 121a and a permission signal outputting unit 121b.

The position determining unit 121a determines whether or not a length by which the distal end part 102 of the endoscopic device 10 is inserted to the inside of the subject exceeds a threshold value corresponding to a position of an organ set in advance based on a result of the calculation input from the UPD device 11. Specifically, the position determining unit 121a determines whether or not the length of the distal end part 102 of the endoscopic device 10 inserted from a specified position (mouth, for example) exceeds a threshold value (a length from a mouth to a stomach or a length from a mouth to a duodenum, for example) set in advance for each organ based on the calculation result input from the UPD device 11.

The permission signal outputting unit 121b outputs the permission signal for permitting the optical measurement to the bio-optical measurement apparatus 3 based on a result of the determination by the position determining unit 121a. Specifically, the permission signal outputting unit 121b outputs to the bio-optical measurement apparatus 3 the permission signal of permitting the optical measurement when the position determining unit 121a determines that the distal end part 102 of the endoscopic device 10 has reached a specified organ, the duodenum for example. Therefore, the control unit 121 including the position determining unit 121a and the permission signal outputting unit 121b serves as a control apparatus that outputs the permission signal to the bio-optical measurement apparatus 3 in the third embodiment.

Figure 11:
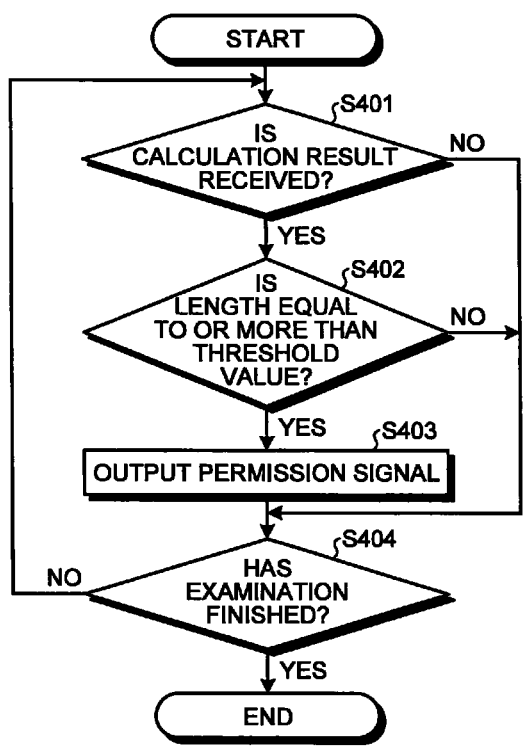
FIG. 11 is a flowchart of an outline of a process performed by a processing device in the endoscope system according to the fourth embodiment of the present invention.

A process performed by the processing device 12 in the endoscope system 300 configured as described above will be explained. FIG. 11 is a flowchart of an outline of a process performed by the processing device 12 in the endoscope system 300.

As shown in FIG. 11, the control unit 121 determines whether or not the calculation result is received from the UPD device 11 (step S401). When the calculation result is received from the UPD device 11 ("Yes" at step S401), the process moves to step S402 to be described later. On the other hand, when the calculation result is not received from the UPD device 11 ("No" at step S401), the process moves to step S404 to be described later.

At step S402, the position determining unit 121a determines whether or not the length by which the distal end part 102 of the insertion unit 101 of the endoscopic device 10 is inserted exceeds the threshold value which indicates the position of the organ set in advance based on the calculation result received from the UPD device 11. When the position determining unit 121a determines that the length of the inserted distal end part 102 of the insertion unit 101 of the endoscopic device 10 exceeds the threshold value ("Yes" at step S402), the processing device 12 moves to step S403. On the other hand, when the position determining unit 121a determines that the length of the inserted distal end part 102 of the insertion unit 101 of the endoscopic device 10 does not exceed the threshold value ("No" at step S402), the processing device 12 moves to step S404 to be described later.

At step S403, the permission signal outputting unit 121b outputs the permission signal of permitting the optical measurement to the bio-optical measurement apparatus 3. In response to the permission signal, the driving controller 327b of the bio-optical measurement apparatus 3 drives the light source unit 321 and the light receiving unit 322 to enable the optical measurement.

The control unit 121 then determines whether or not the endoscopic examination has finished (step S404). When the control unit 121 determines that the endoscopic examination has finished ("Yes" at step S404), the processing device 12 ends the process. On the other hand, when the control unit 121 determines that the endoscopic examination has not finished ("No" at step S404), the processing device 12 returns to step S401.

According to the fourth embodiment of the present invention described above, the permission signal outputting unit 121b outputs the permission signal of permitting the optical measurement to the bio-optical measurement apparatus 3 when the position determining unit 121a determines that the length of the inserted distal end part 102 of the insertion unit 101 of the endoscopic device 10 exceeds the threshold value. Thus, it is possible to automatically perform a measurement only at an appropriate site in a biological body and to surely prevent a human error.

While the optical measurement is enabled by driving the light source unit 321 and the light receiving unit 322 of the bio-optical measurement apparatus 3 when the driving controller 327b receives the permission signal for the measurement in the fourth embodiment, a flag to the effect that a computing result of the optical measurement obtained by the calculation unit 327a is valid may be added and recorded in the recording unit 325. Thus, it is possible to determine whether or not the measurement is performed at an appropriate site in a case where an operator performs a medical examination of a subject by using the measurement result of the bio-optical measurement apparatus 3 at a different site.

While the position determining unit 121a and the permission signal outputting unit 121b are provided in the control unit 121 of the processing device 12 in the fourth embodiment, they may be provided in the bio-optical measurement apparatus 3. This configuration allows surely performing the measurement at an appropriate site only by the bio-optical measurement apparatus 3.

While the position determining unit 121a determines whether or not the distance of the inserted distal end part 102 of the insertion unit 101 of the endoscopic device 10 exceeds the threshold value in the fourth embodiment, a determination of whether or not, for example, a shape of the distal end part 102 becomes a shape indicating an organ set in advance may be made.

Fifth Embodiment

A fifth embodiment of the present invention will be explained next. An endoscope system according to the fifth embodiment includes respective ID information recording units that record ID information at a connector part of a measurement probe and a connector part of an insertion unit of an endoscopic device, and a reader that reads the ID information. Therefore, after a configuration of a control apparatus of an endoscope system and a bio-optical measurement apparatus according to the fifth is explained, a process performed by the endoscope system according to the fifth embodiment will be explained. The same component is assigned with the same reference symbol in the explanation.

Figure 12:
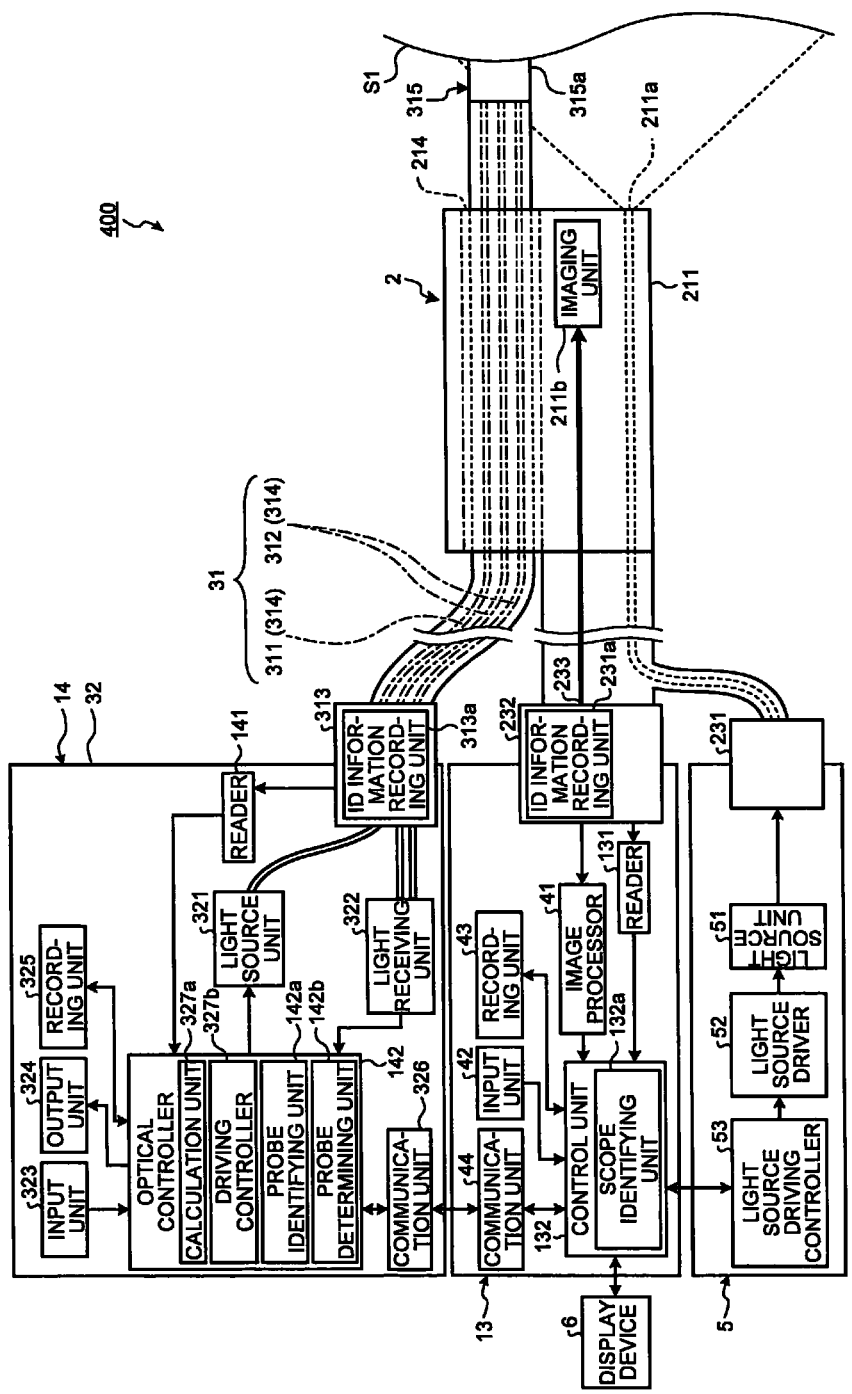
FIG. 12 is a block diagram showing a pattern of a configuration of an endoscope system according to a fifth embodiment of the present invention.

FIG. 12 is a block diagram showing a pattern of a configuration of an endoscope system 400 according to the fifth embodiment. As shown in FIG. 12, the endoscope system 400 includes the illumination device 5, a processing device 13, and a bio-optical measurement apparatus 14.

The processing device 13 includes the image processor 41, the input unit 42, the recording unit 43, the communication unit 44, a reader 131, and a control unit 132.

The reader 131 is configured by using, for example, a barcode reader, a QR code reader, and the like, reads ID information of the endoscopic device 2 (hereinafter referred to as "scope ID") from an ID information recording unit 231a (barcode and QR code) attached to the connector part 232, and outputs the read ID information of the endoscopic device 2 to the control unit 132. Here, the scope ID indicates information of examination item, corresponding organ, type, and model of the endoscopic device 2 which can be used for the subject.

The control unit 132 is configured by using a CPU and the like and controls each unit of the processing device 13. The control unit 132 includes a scope identifying unit 132a.

The scope identifying unit 132a identifies a corresponding organ and an examination item of the endoscopic device 2 which can be used for the subject based on the scope ID input from the reader 131 and outputs a result of the identification to the bio-optical measurement apparatus 14 via the communication unit 44 and the communication unit 326.

The bio-optical measurement apparatus 14 includes the light soured unit 321, the light receiving unit 322, the input unit 323, the output unit 324, the recording unit 325, the communication unit 326, a reader 141, and an optical controller 142.

The reader 141 is configured by using, for example, a barcode reader, a QR code reader, and the like, reads ID information of the measurement probe 31 (hereinafter referred to as "probe ID") from an ID information recording unit 313a (barcode and QR code) attached to the connector part 313, and outputs the read ID information of the measurement probe 31 to the optical controller 142. Here, the probe ID indicates information of examination item, corresponding organ, type, and model of the measurement probe 31 which can be used for the subject.

The optical controller 142 is configured by using a CPU and the like and controls each unit of the bio-optical measurement apparatus 14. The optical controller 142 includes the calculation unit 327a, the driving controller 327b, a probe identifying unit 142a, and a probe determining unit 142b.

The probe identifying unit 142a identifies a corresponding organ and an examination item of the measurement probe 31 which can be used for the subject based on the ID information of the measurement probe 31 input from the reader 141 and outputs a result of the identification to the probe determining unit 142b.

The probe determining unit 142b determines whether or not the measurement probe 31 can support the endoscopic device 2 based on the scope ID and the probe ID. Specifically, the probe determining unit 142b determines whether or not the examination item of the endoscopic device 2 matches the examination item of the measurement probe 31 based on the scope ID and the probe ID.

Figure 13:
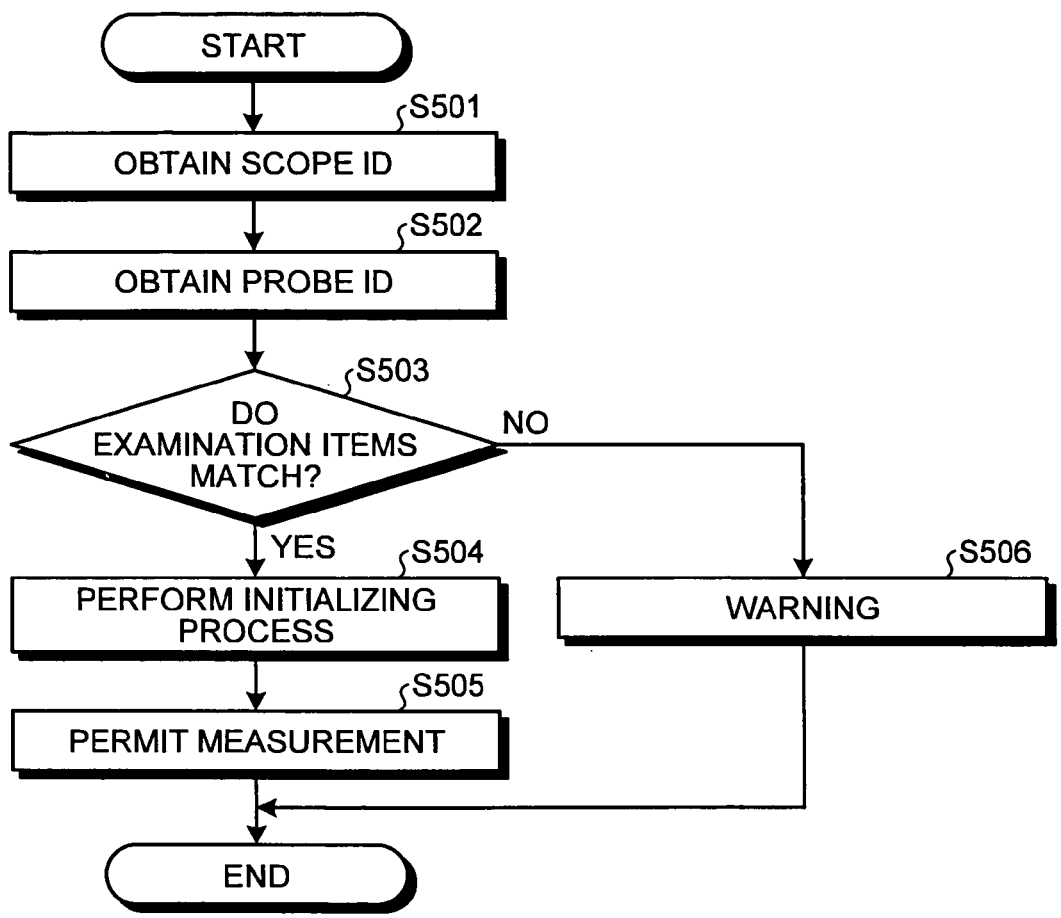
FIG. 13 is a flowchart of an outline of a process performed by a bio-optical measurement apparatus in the endoscope system according to the fifth embodiment of the present invention.

A process performed by the bio-optical measurement apparatus 14 in the endoscope system 400 configured as described above will be explained. FIG. 13 is a flowchart of an outline of a process performed by the bio-optical measurement apparatus 14 in the endoscope system 400.

As shown in FIG. 13, the control unit 142 obtains the scope ID from the processing device 13 via the communication unit 44 and the communication unit 326 (step S501) and obtains the probe ID (step S502).

The probe determining unit 142b then determines whether or not the examination item of the endoscopic device 2 and the examination item of the measurement probe 31 match based on the scope ID and the probe ID (step S503). When the probe determining unit 142b determines that the examination items match ("Yes" at step S503), the driving controller 327b performs an initializing process (step S504). Specifically, the driving controller 327b performs a calibration process in which a white balance and the like of the measurement probe 31 are adjusted.

After that, the driving controller 327b permits the measurement of the bio-optical measurement apparatus 14 (step S505). Specifically, the driving controller 327b enables the measurement of the bio-optical measurement apparatus 14 by driving the light source unit 321 and the light receiving unit 322. After step S505, the bio-optical measurement apparatus 14 ends the process.

When the probe determining unit 142b determines that the examination items do not match at step S503 ("No" at step S503), the driving controller 327b controls the output unit 324 to indicate a warning (step S506). The bio-optical measurement apparatus 14 then ends the process.

According to the fifth embodiment of the present invention described above, the driving controller 327b performs a control of enabling the optical measurement by the bio-optical measurement apparatus 14 when the probe determining unit 142b determines that the scope ID and the probe ID match. Thus, it is possible to surely prevent the measurement probe 31 from wrongly being used since there is no possibility of using the endoscopic device 2 and the measurement probe 31 in different combinations.

While ID information from respective ID information recording units attached to the connector parts is read and then the determination of whether or not to match the examination items of the endoscopic device 2 and the measurement probe 31 is made in the fifth embodiment, the determination may be made depending on a shape of the connector part, for example. A determination of whether or not to match the examination items may be made by changing the shape of the connector part for each examination item, for example. In this case, an examination item (for an upper part use or a lower part use, for example) may be associated with the number of pins (protrusions) as a shape of a connector part.

Sixth Embodiment

A sixth embodiment of the present invention will be explained next. An endoscope system according to the sixth embodiment has a difference in the configuration of the bio-optical measurement apparatus in the endoscope system described above. Therefore, a configuration of a bio-optical measurement apparatus in an endoscope system according to the sixth embodiment will be explained below. The same component is assigned with the same reference symbol in the explanation.

Figure 14:
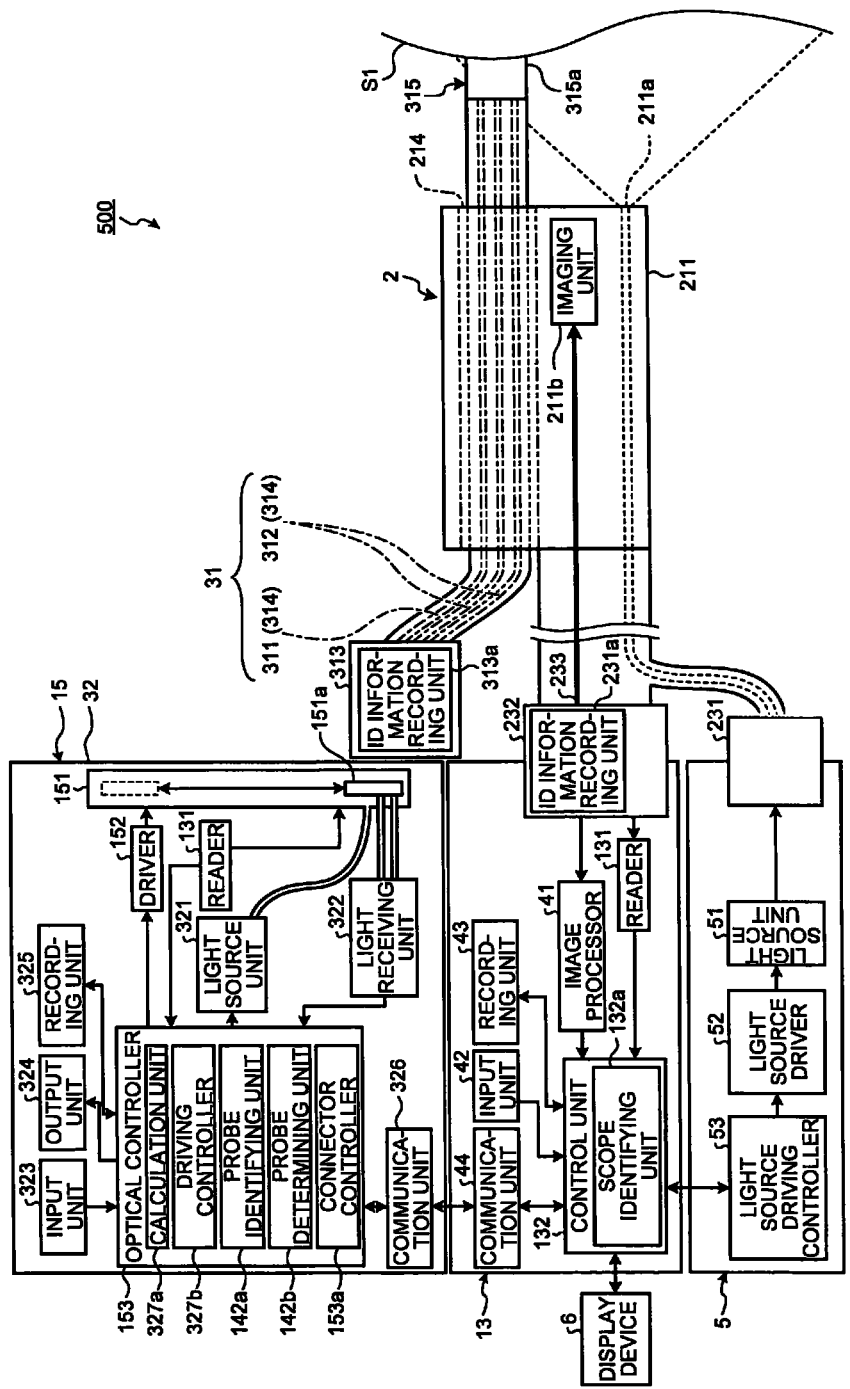
FIG. 14 is a block diagram showing a pattern of a configuration of an endoscope system according to a sixth embodiment of the present invention.

FIG. 14 is a block diagram showing a pattern of a configuration of an endoscope system 500 according to the sixth embodiment. As shown in FIG. 14, the endoscope system 500 includes a bio-optical measurement apparatus 15.

The bio-optical measurement apparatus 15 includes the light source unit 321, the light receiving unit 322, the input unit 323, the output unit 324, the recording unit 325, a switching unit 151, a driver 152, and an optical controller 153.

The switching unit 151 switches a connection of the measurement probe 31. Specifically, the switching unit 151 includes a plate 151a which can move in line to and from a position to which the measurement probe is connected, and bans the connection of the measurement probe 31 when the plate 151a is driven by the driver 152 in the vertical direction.

The driver 152 is realized by using a stepping motor, a DC motor, and the like and drives the switching unit 151 under the control of the optical controller 153.

The optical controller 153 is realized by using a CPU and the like and controls each unit of the bio-optical measurement apparatus 15. The optical controller 153 includes the calculation unit 327a, the driving controller 327b, the probe identifying unit 142a, the probe determining unit 142b, and a connector controller 153a.

The connector controller 153a drives and controls the driver 152 into a state where the connector part 313 of the measurement probe 31 can be connected to the bio-optical measurement apparatus 15. Specifically, the connector controller 153a drives the plate 151a of the switching unit 151 to the upper direction by driving the driver 152 when receiving the scope ID from the processing device 13. Thus, it becomes possible to connect the connector part 313 of the measurement probe 31 to the bio-optical measurement apparatus 15.

According to the sixth embodiment of the present invention described above, the connection of the measurement probe 31 to the bio-optical measurement apparatus 15 is banned until the endoscopic device 2 is connected to the processing device 13. This configuration allows surely preventing a wrong connection of the measurement probe 31 since the connection is physically impossible no matter how many tries are made to connect the measurement probe 31 in wrong combinations.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control apparatus that controls a bio-optical measurement apparatus which is configured to be inserted into a subject through an endoscopic device and is configured to perform an optical measurement of a biological tissue in the subject, the endoscopic device being configured to capture, by inserting a distal end part of the endoscopic device into the subject, in-vivo images of the subject by an imaging unit provided at the distal end part, the control apparatus, comprising:

a position determining unit (i) configured to determine a position of the distal end part in the subject and (ii) configured to determine whether or not the distal end part reaches a specified organ in the subject by using image information of a characteristic part of a boundary of an organ an set in advance in each organ, with respect to the in-vivo images; and a permission signal outputting unit (i) configured to output a permission signal for permitting the optical measurement to the bio-optical measurement apparatus based on a determination result by the position determining unit and (ii) configured to output the permission signal to the bio-optical measurement apparatus when the position determining unit determines that the distal end part reaches the specified organ.

2. The control apparatus according to claim 1, wherein the position determining unit determines the position of the distal end part in the subject based on the in-vivo images.

3. The control apparatus according to claim 1, wherein
the position determining unit determines whether or not a wavelength component which is specific to an organ as a measurement target included in the in-vivo images when a narrow band light is emitted by the endoscopic device exceeds a threshold value set in advance, and
the permission signal outputting unit outputs the permission signal to the bio-optical measurement apparatus when the position determining unit determines that the wavelength component exceeds the threshold value.

4. The control apparatus according to claim 1, wherein
the position determining unit determines whether or not a length of the distal end part inserted into the subject exceeds a threshold value corresponding to a position of an organ set in advance, and
the permission signal outputting unit outputs the permission signal to the bio-optical measurement apparatus when the position determining unit determines that the inserted length exceeds the threshold value.

5. A bio-optical measurement apparatus, comprising:
the control apparatus according to claim 1; and
a driving controller configured to control driving of the bio-optical measurement apparatus when accepting an input of the permission signal from the permission signal outputting unit.

6. An endoscope system, comprising:
an endoscopic device configured to capture, by inserting a distal end part of the endoscopic device into a subject, in-vivo images of the subject by an imaging unit provided at the distal end part; and a bio-optical measurement apparatus that is configured to be inserted into the subject through the endoscopic device and is configured to perform an optical measurement of a biological tissue in the subject, wherein
the endoscopic device comprises:
a position determining unit (i) configured to determine a position of the distal end part in the subject and (ii) configured to determine whether or not the distal end part reaches a specified organ in the subject by using image information of a characteristic part of a boundary of an organ set in advance in each organ, with respect to the in-vivo images; and
a permission signal outputting unit (i) configured to output a permission signal for permitting the optical measurement to the bio-optical measurement apparatus based on a determination result by the position determining unit and (ii) configured to output the permission signal to the bio-optical measurement apparatus when the position determining unit determines that the distal end part reaches the specified organ.

7. The endoscope system according to claim 6, wherein the position determining unit determines the position of the distal end part in the subject based on the in-vivo images.

8. The endoscope system according to claim 6, wherein
the position determining unit determines whether or not a wavelength component which is specific to an organ as a measurement target included in the in-vivo images when a narrow band light is emitted by the endoscopic device exceeds a threshold value set in advance, and
the permission signal outputting unit outputs the permission signal to the bio-optical measurement apparatus when the position determining unit determines that the wavelength component exceeds the threshold value.

9. The endoscope system according to claim 6, wherein
the position determining unit determines whether or not a length of the distal end part inserted into the subject exceeds a threshold value corresponding to a position of an organ set in advance, and
the permission signal outputting unit outputs the permission signal to the bio-optical measurement apparatus when the position determining unit determines that the inserted length exceeds the threshold value.

10. The endoscope system according to claim 6, further comprising a driving controller configured to control driving of the bio-optical measurement apparatus when accepting an input of the permission signal from the permission signal outputting unit.

* * * * *